United States Patent
Berger et al.

(10) Patent No.: US 7,211,785 B1
(45) Date of Patent: May 1, 2007

(54) SCANNING APPARATUS

(75) Inventors: Amir Berger, Kiryat Bialik (IL); Moshe B. Haim, Yokneam (IL); Sergey Zaslavasky, Yokneam (IL)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 11/355,820

(22) Filed: Feb. 16, 2006

(51) Int. Cl.
*H01J 3/00* (2006.01)
*G03B 42/00* (2006.01)

(52) U.S. Cl. .................. 250/228; 250/234; 250/586

(58) Field of Classification Search ............. 250/228, 250/234, 236, 584–586; 378/62, 70
See application file for complete search history.

(56) References Cited

U.S. PATENT DOCUMENTS

| | | | |
|---|---|---|---|
| 4,453,180 A | 6/1984 | Juergensen | |
| 4,886,968 A | 12/1989 | Ohnishi et al. | |
| 5,396,081 A | 3/1995 | Ogura et al. | |
| 5,399,877 A | 3/1995 | Carter et al. | |
| 5,598,008 A | 1/1997 | Livoni | |
| 5,635,728 A | 6/1997 | Cantu et al. | |
| 6,291,831 B1 * | 9/2001 | Koren | 250/584 |
| 6,791,101 B2 | 9/2004 | Koren | |

FOREIGN PATENT DOCUMENTS

JP   HEI 6-160311   6/1994

* cited by examiner

*Primary Examiner*—Kevin Pyo
(74) *Attorney, Agent, or Firm*—Susan L. Parulski

(57) ABSTRACT

A scanning apparatus including a cylindrical member and an optical system. The cylindrical member rotates about a rotational axis and has an outer surface to support a storage phosphor sample thereon. The optical system moves in translation parallel to the rotational axis to scan the sample. The optical system comprises an opening, an excitation beam, an integrating member, and a single detector. The excitation beam is directed through the opening to impinge on a sample and cause light to be emitted from the sample. The integrating member reflects the emitted light using an interior three-dimensional polynomial surface providing diffuse reflection. The single detector is disposed adjacent the integrating member for collecting the reflected emitted light.

3 Claims, 3 Drawing Sheets

SCANNING APPARATUS

FIELD OF THE INVENTION

The invention relates generally to an axially oriented optical system, and in particular to a system using a light beam for scanning a medium.

BACKGROUND OF THE INVENTION

The field of computed radiography (CR) is well known in the medical area. With CR, a storage phosphor plate has a radiographic image formed thereon by exposing an object (such as a body part), to x-rays. The exposed storage phosphor plate is then provided to a reader/scanner where the plate is stimulated with radiation if one light frequency to email a radiation image of another light frequency. The emitted image is captured, converted to a digital radiograph I image, and stored, displayed or otherwise used.

Scanners of x-ray exposed storage phosphor plates can perform their function on a flat-bed or an external surface of a rotating drum. Such radiation image readout apparatus are known, for example, refer to U.S. Pat. No. 4,886,968 (Ohnishi), U.S. Pat. No. 5,396,081 (Ogura), and U.S. Pat. No. 5,635,728 (Cantu), and U.S. Pat. No. 6,791,101 (Koren).

Optical systems for such scanning apparatus are known. For example, JP Unexamined Patent Publication No. Hei 6-160311 is directed to a radiation image reading apparatus. U.S. Pat. No. 4,453,180 (Juergensen) is directed to a light pick-up device. U.S. Pat. No. 5,399,877 (Carter) is directed to a radiation sensitive area detection device and method. U.S. Pat. No. 5,598,008 (Livoni) is directed to a wavelength selective light collector system.

While such systems may have achieved certain degrees of success in their particular applications, there is a for an optical system of a scanning apparatus which provides improved light collection efficiency, is compact in size, and includes a reduced number of elements.

There is needed an optical system for scanning storage phosphor plates which provides an increase in accuracy and quality.

SUMMARY OF THE INVENTION

An object of the present invention is to provide a scanning apparatus including an optical system.

Another object of the present invention is to provide such a scanning apparatus which is compact in size.

A further object of the present invention is to provide such a scanning apparatus which is suitable for use in a computed radiography reader/scanner.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a scanning apparatus including a cylindrical member and an optical system. The cylindrical member is rotatable about a rotational axis and has an outer surface adapted to support a storage phosphor sample thereon. The optical system is disposed proximate the outer surface and is movable in translation in a direction substantially parallel to the rotational axis of the cylindrical member to scan the sample. The optical system comprises an opening, an excitation beam, an integrating member, and a single detector. The excitation beam is directed along a first axis through the opening to impinge on a sample and cause light to be emitted from the sample, wherein the first axis is orthogonal to the rotational axis. The integrating member reflects the emitted light using an interior three-dimensional polynomial surface providing diffuse reflection. The opening is disposed adjacent the outer surface through which the excitation beam is directed to impinge the sample. The single detector is disposed adjacent the integrating member for collecting the reflected emitted light, the single detector disposed along an axis substantially parallel to the rotational axis.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
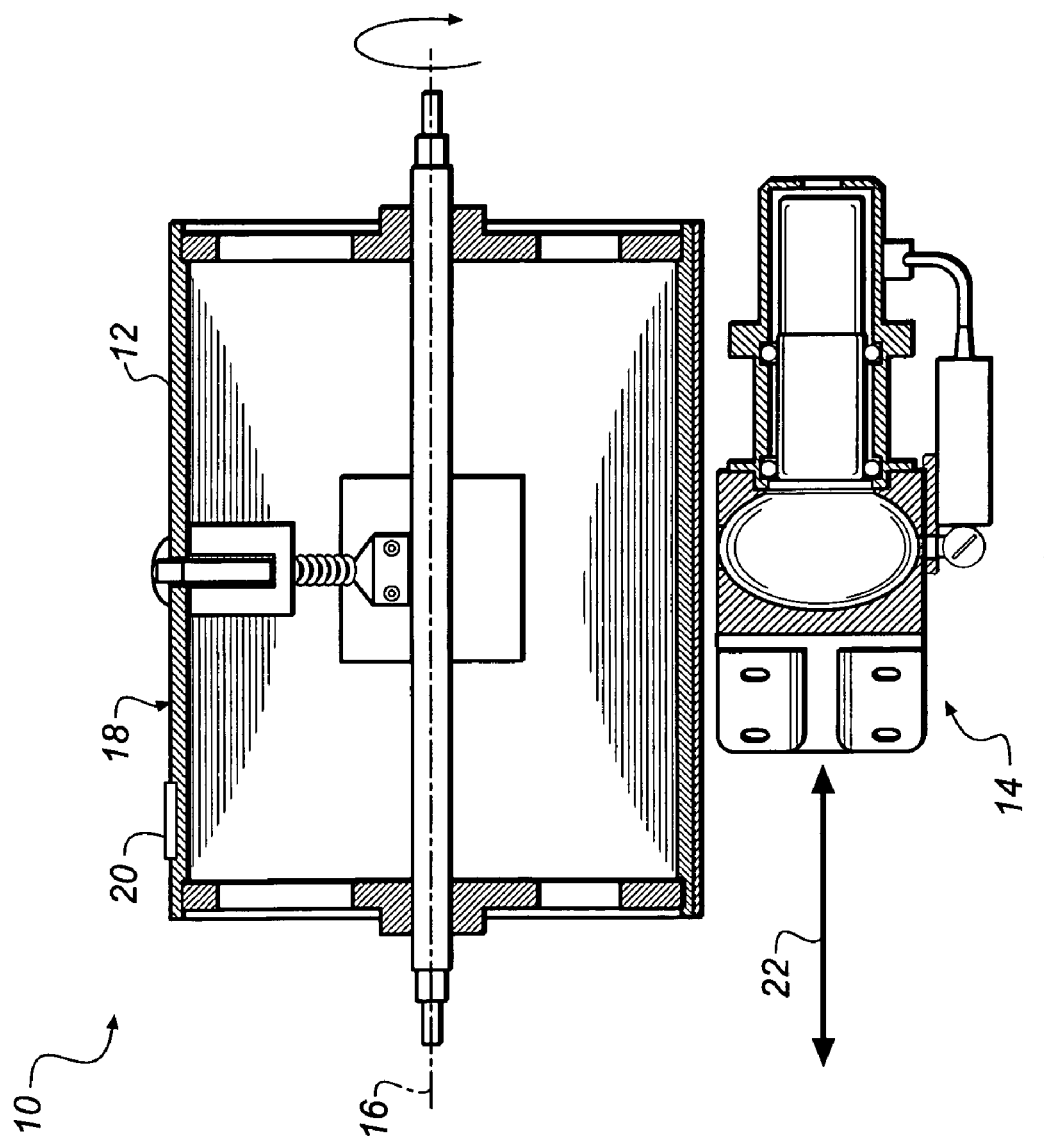
FIG. 1 shows a diagrammatic cross-sectional view of a scanning apparatus in accordance with the present invention.

The following is a detailed description of the preferred embodiments of the invention, reference being made to the drawings in which the same reference numerals identify the same elements of structure in each of the several figures.

The present invention is directed to a scanning apparatus including an axially oriented optical system.

Referring to FIG. 1, there is shown a scanning apparatus 10 including a cylindrical member 12 and a optical system 14. Cylindrical member 12 is rotatable about a rotational axis 16.

Cylindrical member 12 includes an outer surface 18 which can support one or more storage phosphor samples 20, of which the samples can be the same size or of different sizes. Samples 20 are stationarily secured to outer surface 18, and optical system 14 moves in translation in a direction 22 substantially parallel to rotational axis 16 so as to scan sample 20.

Figure 2:
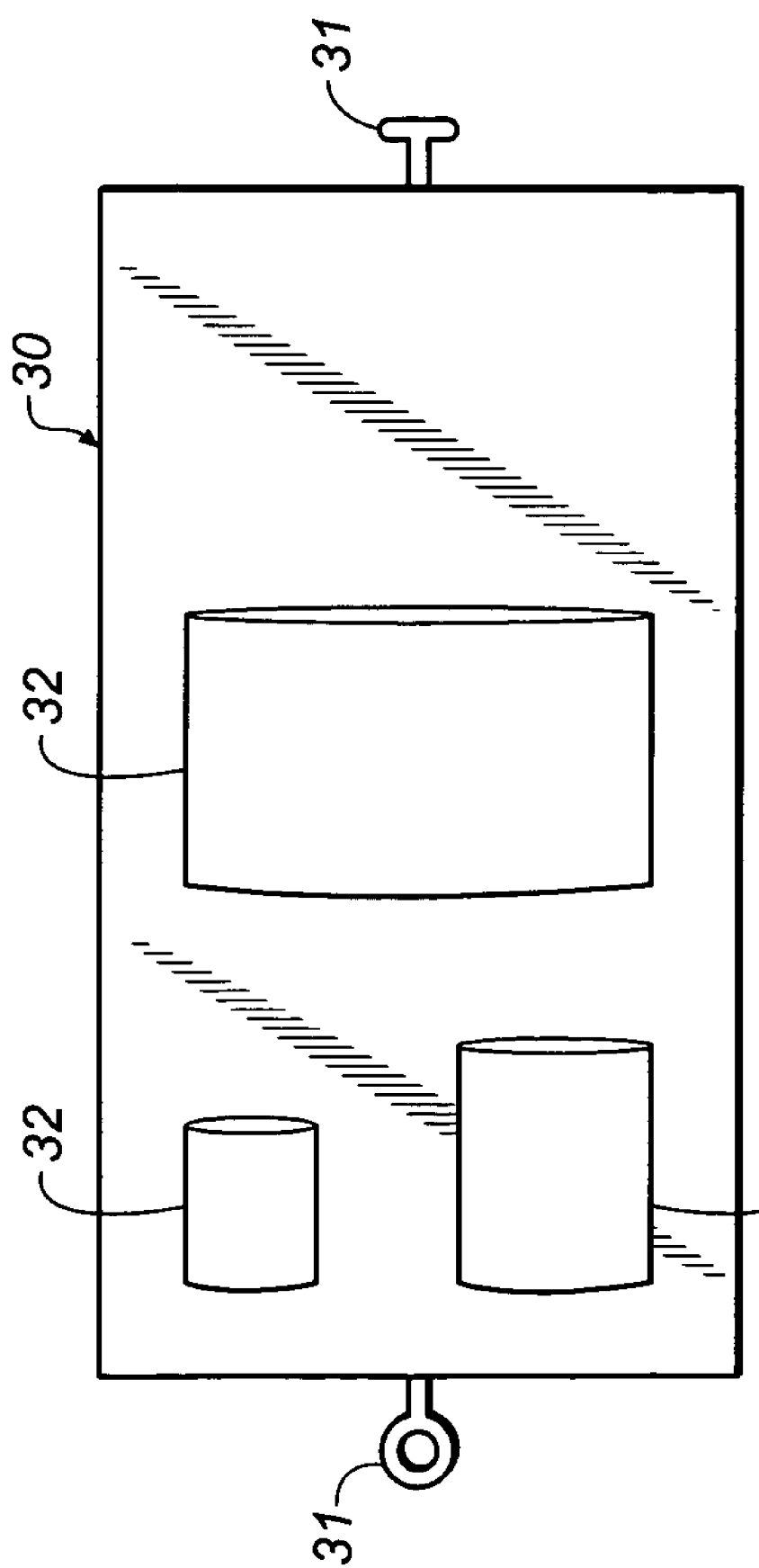
FIG. 2 shows a diagrammatic view of an exemplary holder for securing samples to a cylindrical member.

Means for attaching and detaching the samples to outer surface 18 can be accomplished by means known to those skilled in the art. For example, FIG. 2 shows a holder/template 30 having an member 31 for attaching/detaching holder 30 to/from cylindrical member 12. Holder 30 can includes pockets or slots 32 sized for receiving samples 20. Alternatively, pockets 32 can be directly attached to outer surface 18.

Figure 3:
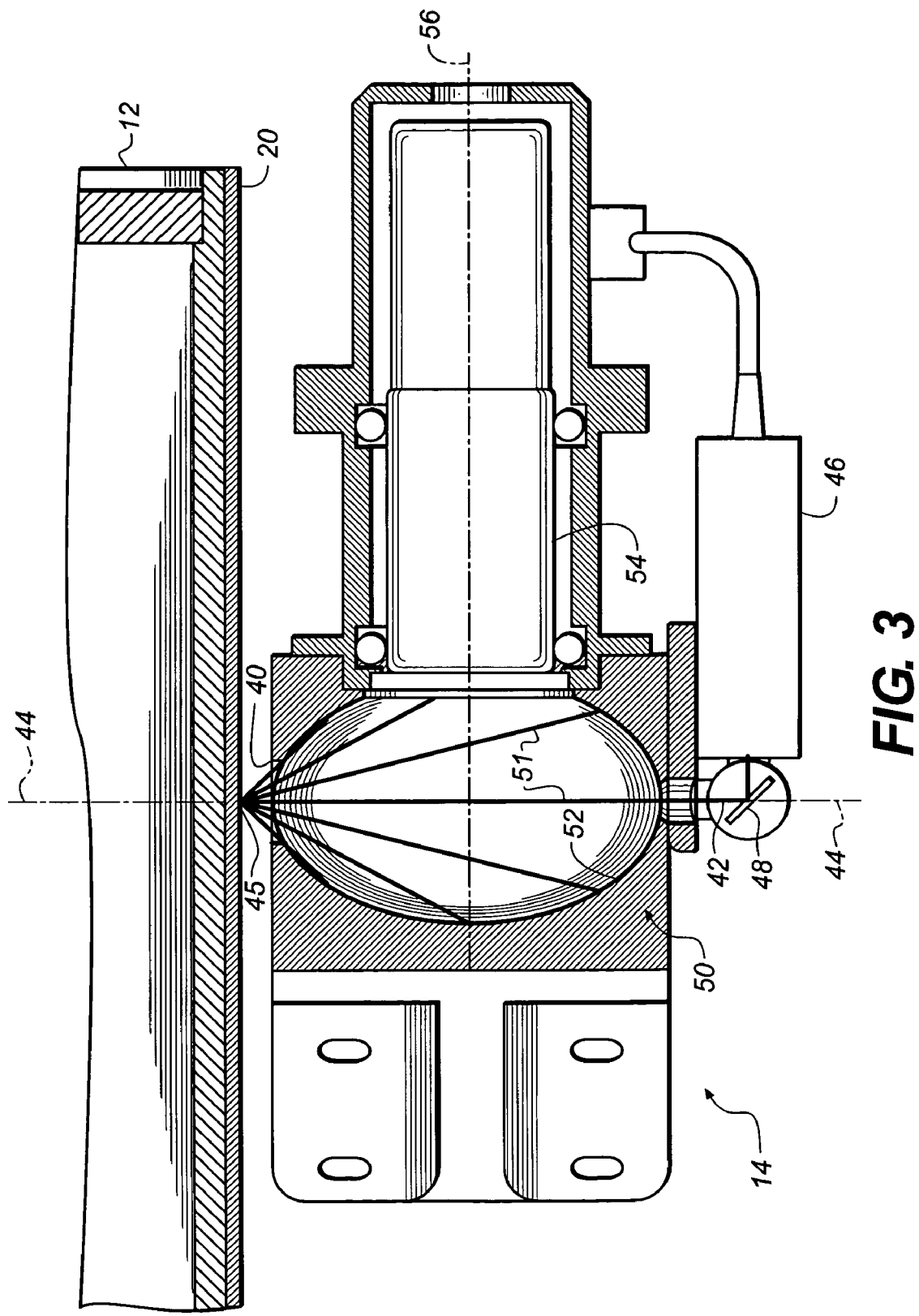
FIG. 3 shows a diagrammatic cross-sectional view of the scanning apparatus of FIG. 1 more particularly illustrating the optical system in accordance with the present invention.

FIG. 3 is provided to more particularly describes optical system 14. As illustrated in FIG. 3, sample 20 is supported on outer surface 18 of cylindrical member 12 such that optical system 14 is disposed proximate sample 20. Optical system 14 includes an opening 40 facing sample 20. An excitation beam 42 is directed along a first axis 44 through opening 40 so as to impinge on sample 20 and cause light to be emitted from sample 20. The impingement of excitation beam 42 on sample 20 is shown in FIG. 3 at 45.

As is known to those skilled in the art, excitation beam 42 can be a laser beam or other form or light emitted from a source 46 which is suitable for stimulating the storage phosphor of sample 20.

As illustrated in FIG. 3, first axis 44 is orthogonal to rotational axis 16. Excitation beam 42 can be directed directly along first axis 44. Alternatively, as shown in FIG. 3, excitation beam 42 can be bent by a reflective member 48 (such as a mirror) from a second axis which is not parallel to first axis 44. Bending the excitation beam can provide for a more compact arrangement of optical system 14.

Optical system 14 further includes an integrating member 50 for collecting and reflecting the light emitted from sample 20. The reflected light is shown in FIG. 3 as rays 51. An interior surface 52 of integrating member 50 is defined by a three-dimensional polynomial shape. Interior surface 52 is more particularly defined as an ellipsoid wherein one of its focal points is a laser impinging point on sample 20.

Interior surface 52 provides diffuse reflection. That is, interior surface 52 is comprised of a material/coating/layer which is diffused. Such reflective materials are commercially available, for example, Barium Sulfide, "Spectralon" or Spectralact Coating appearing as a diffused white surface having good diffused reflectance properties. This diffused surface provides the integrating member with the ability to sum the light entering the member without dependency on the energy profile making the image uniform including the edges.

It is noted that excitation beam 42 is directed through integrating member 50 along first axis 44 through opening 40 so as to impinge sample 20.

Optical system 1 further includes a single detector 54 disposed adjacent integrating member 50 for collecting the reflected emitted light. As is shown in FIG. 3, detector 54 is disposed along an axis 56 which is substantially parallel to rotational axis 16. As such, a face of detector 54 is arranged substantially perpendicular to opening 40.

As is known to those skilled in the art, detector 54 can be a photo multiplier tube which converts the light emitted from the sample into electric signals.

As shown in FIG. 3, opening 40 of optical system 14 faces sample 20. Opening 40 can be, for example, a small (e.g., round) hole of a size defined by the assumption that the light emitted from the impinging point has a Lambetian shape therefore trying to collect a maximum (e.g., 98%) of the light requires collecting angel of 114 degrees therefore the diameter is defined by the distance of the opening from the impinging point surface.

Minimal spacing is needed between optical system 14 and sample 20. In one arrangement, optical system 14 is spaced from the storage phosphor sample by no more than 7 mm when the storage phosphor sample is disposed on the outer surface. In a preferred arrangement, optical system 14 is spaced from the storage phosphor sample by about 3 mm when the storage phosphor sample is disposed on the outer surface.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. A scanning apparatus, comprising:
   a cylindrical member rotatable about a rotational axis and having an outer surface adapted to support a storage phosphor sample thereon; and
   an optical system disposed proximate the outer surface and translatable in a direction substantially parallel to the rotational axis of the cylindrical member to scan the sample, the optical system comprising:
   (a) an opening;
   (b) an excitation beam is directed along a first axis through the opening to impinge on a sample and cause light to be emitted from the sample, the first axis being orthogonal to the rotational axis;
   (c) an integrating member reflecting the emitted light, the integrating member having an interior three-dimensional polynomial surface providing diffuse reflection, the excitation beam being directed through the integrating member along the first axis through the opening to impinge the sample; and
   (d) a single detector disposed adjacent the integrating member for collecting the reflected emitted light, the single detector disposed along an axis substantially parallel to the rotational axis.

2. The scanning apparatus of claim 1, wherein the optical system is spaced from the storage phosphor sample by no more than 7 mm when the storage phosphor sample is disposed on the outer surface.

3. The scanning apparatus of claim 1, wherein the optical system is spaced from the storage phosphor sample by about 3 mm when the storage phosphor sample is disposed on the outer surface.

* * * * *